United States Patent
Burdeniuc

(10) Patent No.: US 6,573,379 B2
(45) Date of Patent: Jun. 3, 2003

(54) METHOD FOR PREPARING HALOMETHYL HETEROCYCLIC COMPOUNDS

(75) Inventor: Juan Jesus Burdeniuc, Macungie, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 10/247,121

(22) Filed: Sep. 19, 2002

(65) Prior Publication Data

US 2003/0050475 A1 Mar. 13, 2003

Related U.S. Application Data

(62) Division of application No. 09/909,000, filed on Jul. 19, 2001, now Pat. No. 6,492,517.

(51) Int. Cl.[7] .............................................. C07D 241/42

(52) U.S. Cl. ..................... 544/353; 546/108; 546/180; 548/257; 548/306.4

(58) Field of Search ......................................... 544/353

(56) References Cited

U.S. PATENT DOCUMENTS

| | | | | |
|---|---|---|---|---|
| 3,960,963 | A | 6/1976 | Gavin | 260/582 |
| 4,845,226 | A | 7/1989 | Hagen et al. | 546/180 |
| 5,183,825 | A | 2/1993 | Kees | 514/404 |
| 5,217,977 | A | 6/1993 | Crawley et al. | 514/311 |
| 6,117,873 | A | 9/2000 | Acklin et al. | 514/249 |
| 6,211,196 | B1 | 4/2001 | Heitsch et al. | 514/311 |
| 6,251,913 | B1 | 6/2001 | Bird | 514/259 |

FOREIGN PATENT DOCUMENTS

| | | |
|---|---|---|
| DE | 292452 | 6/1990 |
| EP | 0257518 | 8/1987 |
| EP | 0260744 | 9/1987 |
| WO | WO 98/43959 | 10/1998 |

OTHER PUBLICATIONS

R. Granger, et al., "Facilitation of Glutamate Receptors Reverses an Age–Associated Memory Impairment in Rats," Synapse, 22, pp. 332–337, 1996.
G. Lynch, et al., "Psychological Effects of a Drug that Facilitates Brain AMPA Receptors," International Clinical Psychopharmacology, 11, pp. 13–19, 1996.
W. F. Gum, "Structure vs. Reactivity in Quinoxalinecarboxylic Acids and Esters", J. Org. Chem. 30, 3982, 1965.
H. Huang, et al., Yixue Yanjiu, 13, 247–54, 1993.
B. Shilling, Ber., 34, pp 902–907, 1901.
A. Tallec, Ann. Chim. (Paris), 3, 164, 1968.
V. Cere, et al.i, Catalytic Hydrogenaton of Benzo [2.1.3] Oxadiazoles, Tetrahedron vol. 28, 3271–3276, Pergamon Press 1972.
M. Hudlicky, "Oxidations in Organic Chemistry," ACS Monograph 186, 1990, p 104–109.
R. A. Sheldon, et al., "Metal–Catalyzed Oxidation of Organic Compounds," Chapter 5, pp. 120–151, Academic Press, 1981.
R. Adams, et al., 2–3–Pyrazinedicarboxylic acid: "Organic Synthesis" Coll. vol. 4, pp. 824–827, J. Wiley & Sons, Inc., NY 1963.
R. A. Sheldon, J. K. Kochi, "Activation by Coordination to Transition Metal Complexes," Chapter 7, pp. 189–214, Academic Press, 1981.
J. C. Cavagnol, et al., "1–Alkyl–1,2,3,4–tetrahydroquinoxalines[1]," J. Am. Chem. Soc., 69, 795, 1947.
Thomas D. Waugh, "NBS: N–Bromosuccinimide—Its Reactions and Uses," Araphoe Chemicals, Inc., Boulder Co. 1951.
Benzoyl Piperadine: "Organic Synthesis", Coll. vol. 1 pp. 108–110, J. Wiley & Sons, Inc. New York, 1943.
R. C. DeSelms, et al., "The Preparations of Some Substituted Quinoxalines and 1,2,3,4–Tetrahydroquinoxalines," J. Het. Chem., vol. 11, pp. 595–597 (1974).
European Search Report, 02015663.4–2101 dated Dec. 10, 2002.
A. R. Katritzky, et al., Synthesis of 5,5–DI–(Benzotriazol–5–Ylmethyl)–2,2–Dimethyl–1,3–Dioxane–04,6–Dione and 5–(Benzotriazol–5–Ylmethyl)–2,2,5–Trimethyl–1,3–Dioxane–4, 6–Dione, Synthetic Communications, Marcel Dekker, Inc., Basel, Ch., vol. 23, No. 14, pp. 2019–2025.
Y. Mikata, et al., Effect of the Linking Position of a Side Chain in Bis(Quinolylmethyl) Ethylenediamine as a DNA Binding Agent, Chemical and Pharmaceutical Bulletin, Pharmaceutical Society of Japan, vol. 48, No. 4, pp. 477–479 (2000).
G. R. Newkome, et al., "Alpha–Methyl Functonalization of Electron–Poor Heterocycles: Free Radical Chlorination," Synthesis, Georg Thieme Verlag,. vol. 8, pp. 676–679 (1984).
J. Finkelstein, et al., "Studies in Phenanthridine Chemistry," Journal of the American Chemical, American Chemical Society, Washington, DC, vol. 73, pp. 302–304 (1951).
V. Rukachaisirikul, et al., "Photolytic Generation of Ketones from 6–Phenanthridinylmethyl Ethers of Secondary Alcohols," Tetrahedron, vol. 48, No. 48, pp. 10563–10568 (1992).

Primary Examiner—Emily Bernhardt
Assistant Examiner—C. Styles
(74) Attorney, Agent, or Firm—Michael Leach

(57) ABSTRACT

The present invention relates to a method for preparing 5- and 6-halomethyl quinoxalines. The method comprises contacting a 5- or 6-methyl quinoxaline with a halogenating agent in the presence of a radical initiator in a solvent selected from the group consisting of fluorobenzene, difluorobenzenes, trifluorobenzenes, chlorobenzene, dichlorobenzenes, trichlorobenzenes, α, α, α-trifluorotoluene and α, α, α-trichlorotoluene. The invention also relates to preparing 6-bromomethyl quinoxaline with N-bromosuccinimide in the presence of a radical initiator in 1,2-dichloroethane. The method for halogenating benzylic methyl groups may also be employed to halogenate a wide variety of halomethyl heterocyclic compounds.

1 Claim, No Drawings

METHOD FOR PREPARING HALOMETHYL HETEROCYCLIC COMPOUNDS

This application is a division of U.S. Ser. No. 09/909,000, filed Jul. 19, 2001, now U.S. Pat. No. 6,492,517.

BACKGROUND OF THE INVENTION

The present invention relates to a method for preparing halomethyl heterocyclic compounds, especially 5- and 6-halomethyl quinoxalines.

The disclosures referred to herein to illustrate the background of the invention and to provide additional detail with respect to its practice are incorporated herein by reference and, for convenience, are numerically referenced in the following text and respectively grouped in the appended bibliography.

Quinoxaline-6-carboxylic acid is an important chemical intermediate for the preparation of compounds such as AMPHAKINE CX516® [1-(quinoxalin-6-ylcarbonyl)piperidine], a drug being tested for the treatment of Alzheimer's disease, Attention Deficit Hyperactivity Disorder (ADHD), Mild Cognitive Impairment (MCI), Chronic Schizophrenia and male sexual dysfunction (1). The preparation of AMPHAKINE CX516® involves the conversion of 3,4-diaminobenzoic acid to quinoxaline-6-carboxylic acid with sodium glyoxal bisulfite, followed by amidation of the resulting acid with piperidine, as set-out below (2, 12).

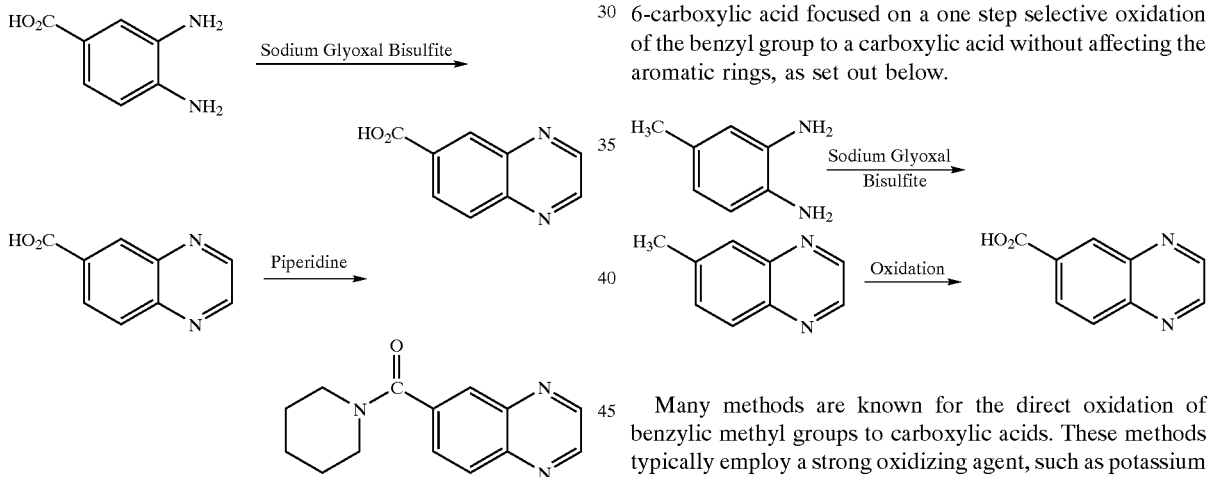

Although the preparation of AMPHAKINE CX516® appears straightforward, the synthesis requires the use of 3,4-diaminobenzoic acid, an expensive starting material. For example, preparation of the isomeric 2,3-diaminobenzoic acid employs a multi-step method that includes oxidation, reduction, amidation, nitration, separation of isomers, further reduction, and hydrolysis, as set out below (3). Preparation of the isomeric 3,4-diaminobenzoic acid can be carried out using this multi-step method by isolating and further reacting the 3-amido, 4-nitrobenzoic acid isomer.

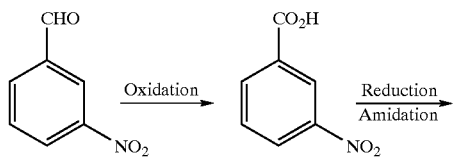

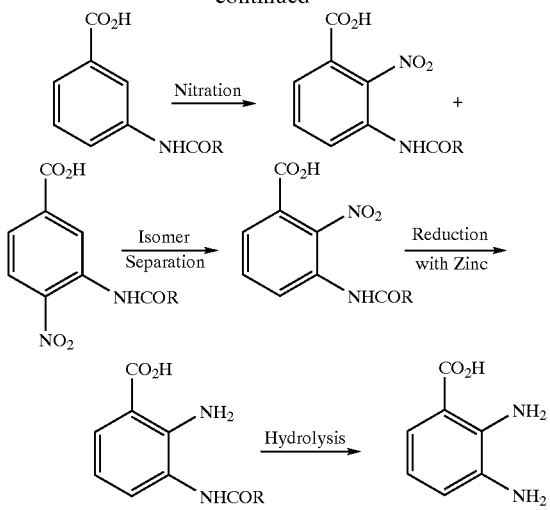

Other methods for preparing 3,4-diaminobenzoic-acid involve the electrochemical reduction of 3,4-dinitrobenzoic acid and the hydrogenation of substituted benzofurazans (4). These methods also employ expensive chemical intermediates.

Initial attempts by the applicant to prepare quinoxaline-6-carboxylic acid focused on a one step selective oxidation of the benzyl group to a carboxylic acid without affecting the aromatic rings, as set out below.

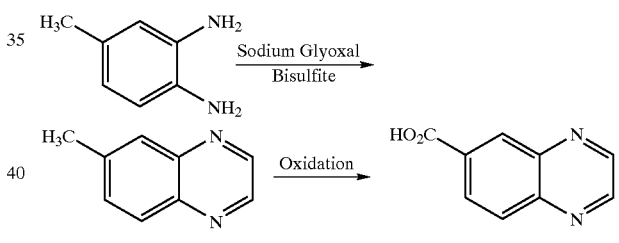

Many methods are known for the direct oxidation of benzylic methyl groups to carboxylic acids. These methods typically employ a strong oxidizing agent, such as potassium permanganate, that reacts with a methyl group providing the remainder of the molecule is not reactive to the oxidizing agent (5). Thus, toluene can be oxidized with potassium permanganate to benzoic acid without affecting the benzene ring (5). Catalytic methods are generally more acceptable for industrial scale because theses methods employ milder oxidizing agents, i.e., air or oxygen, to carry out the oxidation of benzylic methyl groups to the corresponding carboxylic acid (6). The oxidation of 5- and 6-methyl-quinoxalines to 5- and 6-quinoxaline-carboxylic acids is not so straightforward, however, because strong oxidizing agents, such as potassium permanganate, degrade the aromatic ring yielding 2,3-pyrazinedicarboxylic acid (7):

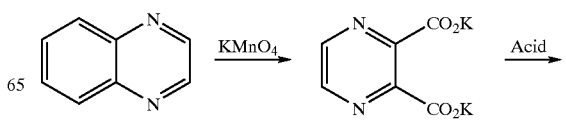

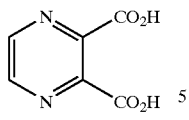

Milder oxidizing agents, i.e., air or oxygen in the presence of a catalyst, on the other hand, have no effect on the benzylic methyl group of 5- or 6-methyl-quinoxaline. Air in the presence of a cobalt salt can oxidize toluene to benzoic acid (6) but does not oxidize methyl-quinoxaline to quinoxaline-carboxylic acid. Similarly, air and oxygen in the presence of a palladium or platinum catalyst are also ineffective (8). Most known oxidizing reagents are either too mild to react with methyl-quinoxalines or are too reactive causing structural changes.

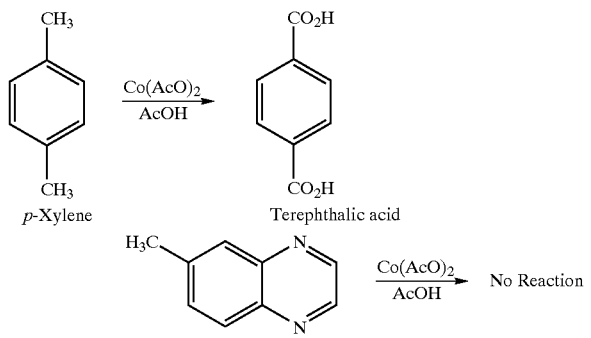

Because attempts to prepare quinoxaline-6-carboxylic acid via a one-step selective oxidation of the benzyl group were not successful, a two-step method to prepare quinoxaline-6-carboxylic acid was developed. In the first step, 6-methyl-quinoxaline is halogenated to provide a 6-halomethyl-quinoxaline intermediate. In the second step, the 6-halomethyl-quinoxaline intermediate is oxidized to the corresponding quinoxaline-6-carboxylic acid.

BRIEF SUMMARY OF THE INVENTION

The present invention relates to a method for preparing 5- and 6-halomethyl quinoxalines (I). The method comprises contacting a 5- or 6-methyl quinoxaline (II) with a halogenating agent in the presence of a radical initiator in a solvent selected from the group consisting of fluorobenzene, difluorobenzenes, trifluorobenzenes, chlorobenzene, dichlorobenzenes, trichlorobenzenes, α, α, α-trifluorotoluene and α, α, α-trichlorotoluene, to form the respective 5- or 6-halomethyl quinoxaline (I). X is a halogen.

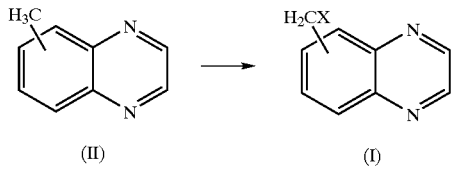

The present invention also pertains to a method for preparing a halomethyl compound selected from the group consisting of:

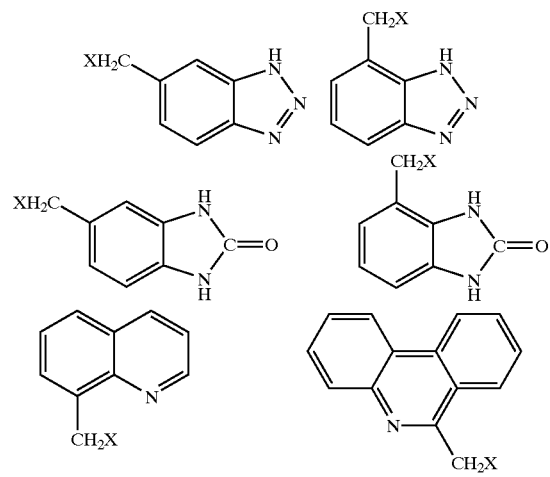

The method comprises contacting the methyl precursor compound of the respective halomethyl compound with a halogenating agent in the presence of a radical initiator in a solvent selected from the group consisting of fluorobenzene, difluorobenzenes, trifluorobenzenes, chlorobenzene, dichlorobenzenes, trichlorobenzenes, α, α, α-trifluorotoluene and α, α, α-trichlorotoluene, to form the respective halomethyl compound, wherein X is a halogen.

The present invention also pertains to a halomethyl compound selected from the group consisting of:

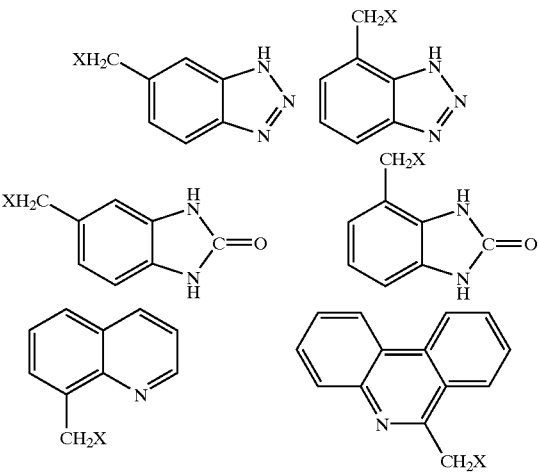

X is a halogen.

The present invention also pertains to a method for preparing 6-bromomethyl quinoxaline. The method comprises contacting 6-methyl quinoxaline with N-bromosuccinimide in the presence of a radical initiator in 1, 2-dichloroethane to form 6-bromomethyl quinoxaline.

DETAILED DESCRIPTION OF THE INVENTION

The present invention pertains to a two-step method for converting benzyl heterocyclic compounds to the corresponding carboxylic acid heterocyclic compounds. The two-step method is especially suitable for converting 5- and 6-benzyl quinoxalines to the corresponding quinoxaline-5- and 6-carboxylic acids. The 5- and 6-benzyl quinoxalines may be prepared from ortho-diaminotoluenes, such as 2,3- and 3,4-diaminotoluene, by condensation with sodium glyoxal bisulfite. The method for halogenating benzylic methyl groups may also be employed to halogenate a wide variety of heterocyclic compounds.

In the first step, 6-methyl-quinoxaline is halogenated to provide a 6-halomethyl-quinoxaline intermediate.

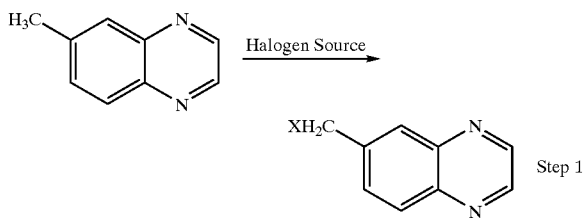

In the second step, the 6-halomethyl-quinoxaline intermediate is oxidized to the corresponding quinoxaline-6-carboxylic acid.

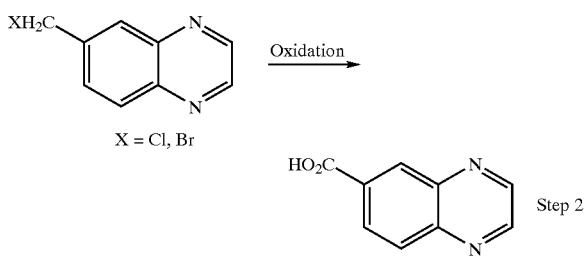

This second step is more fully described in a copending patent application entitled "Method For Preparing Heterocyclic-Carboxylic Acids" filed by applicant concurrently with the present patent application and assigned to the assignee of this application, which is hereby incorporated by reference.

As set out above, 5- and 6-benzyl quinoxalines may be prepared from ortho-diaminotoluenes, such as 2,3- and 3,4-diaminotoluene, by condensation with sodium glyoxal bisulfite. For example, 6-benzyl quinoxaline may be prepared by condensation of 3,4-diaminotoluene with sodium glyoxal bisulfite (9).

Because attempts to prepare quinoxaline-6-carboxylic acid via a one-step selective oxidation of the benzyl group were not successful, a two-step method to prepare quinoxaline-6-carboxylic acid was developed. In the first step, 6-methyl-quinoxaline is halogenated to provide a 6-halomethyl-quinoxaline intermediate. In the second step, the 6-halomethyl-quinoxaline intermediate is oxidized to the corresponding quinoxaline-6-carboxylic acid.

In the first step of the synthesis, a benzylic heterocyclic compound and a halogenating agent, such as N-chlorosuccinimide (NCS) or N-bromosuccinimide (NBS), are reacted in the presence of a radical initiator, such as benzoyl peroxide or azobisisobutyronitrile, in a suitable solvent, to form the respective halomethyl heterocyclic compound, such as a 5- or 6-halomethyl quinoxaline (I). Suitable solvents may be selected from the group consisting of fluorobenzene, difluorobenzenes, trifluorobenzenes, chlorobenzene, dichlorobenzenes, trichlorobenzenes, α, α, α-trifluorotoluene and α, α, α-trichlorotoluene.

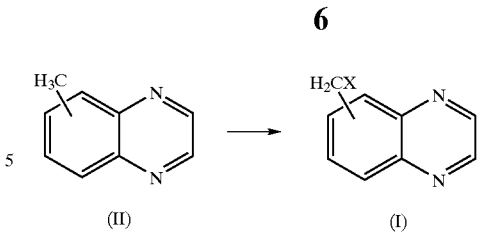

The method for halogenating benzylic positions may also be employed to halogenate a variety of heterocyclic compounds. The method typically affords good yields of halomethyl-quinoxalines when [6QX]/[benzoyl peroxide] $\leq 40$ while maintaining a temperature in the range of 60° C. to 115 °C. for a period of 1 to 12 hours. Yields for benzylic brominations (conversions $\geq 95\%$, selectivities $\geq 97\%$) are in general better than for benzylic chlorinations (conversions 60%, selectivities ~75–80%). The 5- or 6-halomethyl quinoxaline may be a 5-halomethyl quinoxaline or may be a 6-halomethyl quinoxaline. The halomethyl may be a chloromethyl or may be a bromomethyl.

In one preferred embodiment, the invention is directed to a method for preparing 5- and 6-halomethyl quinoxalines (I). The method comprises contacting a 5- or 6-methyl quinoxaline (II) with a halogenating agent in the presence of a radical initiator in a solvent selected from the group consisting of fluorobenzene, difluorobenzenes, trifluorobenzenes, chlorobenzene, dichlorobenzenes, trichlorobenzenes, α, α, α-trifluorotoluene and α, α, α-trichlorotoluene, to form the respective 5- or 6-halomethyl quinoxaline (I), wherein X is a halogen.

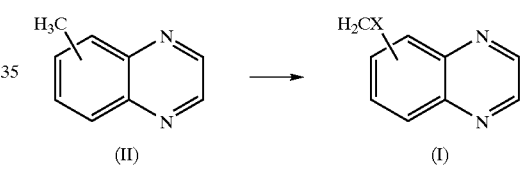

In another preferred embodiment, the invention is directed to a method for preparing a halomethyl compound selected from the group consisting of:

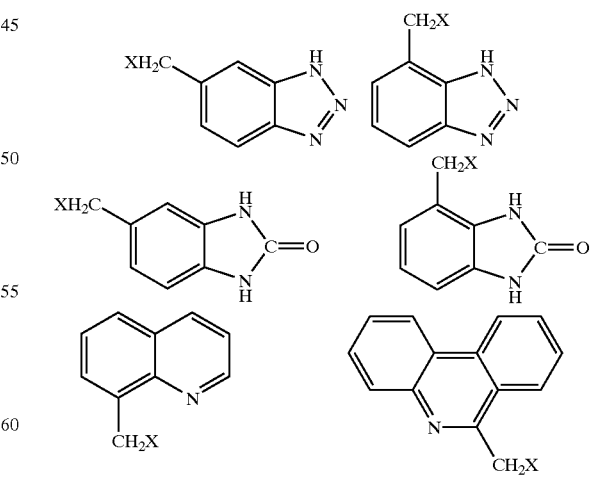

The method comprises contacting the methyl precursor compound of the respective halomethyl compound with a halogenating agent in the presence of a radical initiator in a solvent selected from the group consisting of fluorobenzene, difluorobenzenes, trifluorobenzenes, chlorobenzene, dichlorobenzenes, trichlorobenzenes, α, α, α-trifluorotoluene and α, α, α-trichlorotoluene, to form the respective halomethyl compound, wherein X is a halogen.

Preferably, the halomethyl compound is selected from the group consisting of:

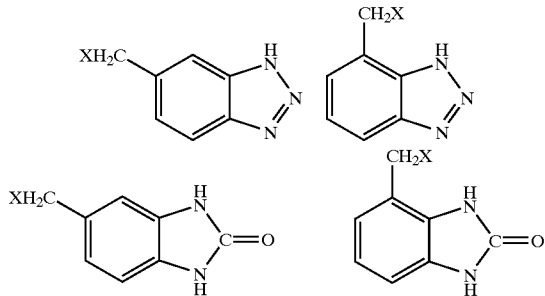

The method comprises contacting the benzyl precursor compound of the respective halomethyl compound with a halogenating agent in the presence of a radical initiator in a solvent selected from the group consisting of fluorobenzene, difluorobenzenes, trifluorobenzenes, chlorobenzene, dichlorobenzenes, trichlorobenzenes, α, α, α-trifluorotoluene and α, α, α-trichlorotoluene, to form the respective halomethyl compound. X is a halogen.

The benzylic halogenation of heterocyclic compounds, such as methyl-quinoxalines, depends on a variety of factors including the halogenating agent, the radical initiator, the solvent, temperature, reaction time, reagent concentrations, and procedure.

The halogenating agents which may be employed in the present invention may be any halogenating agent which is capable of selectively halogenating the benzylic methyl group of a heterocyclic compound. The term "halogen", as used herein, refers to the elements fluorine, chlorine, bromine, and iodine. Preferred halogens are chlorine and bromine. Non-limiting illustrative halogenating agents may be selected from the group consisting of N-chlorosuccinimide, N-bromosuccinimide, $Cl_2$, $Br_2$, t-butyl hypochlorite, N-chloroglutarimide, N-bromoglytarimide, N-chloro-N-cyclohexyl-benzenesulfonimide, and N-bromophthalimide. Preferred halogenating agents are N-chlorosuccinimide and N-bromosuccinimide.

The radical initiators which may be employed in the present invention may be any radical initiator which is capable of catalyzing the halogenating agent to selectively halogenate the benzylic methyl group of a heterocyclic compound. The presence of an initiator is essential for the reaction to occur because radicals propagate these reactions. Non-limiting illustrative radical initiator agents may be selected from the group consisting of benzoyl peroxide, azobisisobutyronitrile (AIBN), diacyl peroxides, dialkyl peroxydicarbonates, tert-alkylperoxyesters, monoperoxycarbonates, di(tert-alkylperoxy)ketals, and ketone peroxides. Preferred radical initiators are benzoyl peroxide and azobisisobutyronitrile. Alternatively, radicals can be generated photochemically.

The solvents which may be employed in the present invention may be any solvent which is capable of promoting the halogenating agent to selectively halogenate the benzylic methyl group of a heterocyclic compound. The choice of solvent is critical. The solvent must (a) be a media in which the halogenating agent has a low, but definite, solubility; (b) be stable to the halogenating agent allowing the halogenating agent to react preferentially at the methyl group of the heterocyclic compound to provide a halomethyl-heterocyclic compound that is stable in the solvent under the reaction conditions; and (c) be environmentally acceptable. Most conventional benzylic bromination procedures employ highly toxic solvents which are rigorously restricted on an industrial level. Suitable solvents may be selected from the group consisting of fluorobenzene, difluorobenzenes, trifluorobenzenes, chlorobenzene, dichlorobenzenes, trichlorobenzenes, α, α, α-trifluorotoluene and α, α, α-trichlorotoluene. Preferred solvents are chlorobenzene and α, α, α-trifluorotoluene.

The temperatures which may be employed in the halogenation reactions of the present invention are important to ensure that the radical initiator decomposes to form radical chain-carriers. Thus, the optimum temperature will depend on the radical initiator used. The temperature should be chosen so that an optimum reaction rate can be reached. Such temperatures may range from about 50° C. to about 120° C., preferably from about 600° C. to about 115° C.

The reaction times which may be employed in the present invention play an important role on the selectivity of the product. Thus, reaction times should be optimum to ensure maximum conversion with best selectivities. Suitable reaction times may range from about 0.5 to about 12 hours, preferably from about 0.75 to about 4 hours. In most cases of benzylic brominations, side-reactions between N-bromosuccinimide (or N-chlorosuccinimide) with the aromatic ring are uncommon. In general, quinoxalines are not expected to react with N-bromosuccinimide and N-chlorosuccinimide by electrophilic aromatic substitution because the quinoxaline ring is known to be resistant to electrophilic attack (13).

The reagent concentrations which may be employed in the present invention may be stoichiometric or may be slightly higher in the halogenating agent concentration used. Although 5-(methyl)-quinoxaline reacted almost to completion in both acetonitrile and acetic acid in the presence of an almost stoichiometric amount of N-bromosuccinimide ([NBS]/[5QX]=1.1), the 6-isomer seems less reactive and does not easily reach completion under similar conditions. Typically, 80% conversion and 94% selectivity for 6-(bromomethyl)-quinoxaline can be accomplished under almost stoichiometric conditions ([NBS]/[5QX]=1.1) but with higher N-bromosuccinimide concentrations (i.e., [NBS]/[5QX]=1.5) yields can be improved (conversion ≧94%, selectivity ≧97%) to reach almost completion.

Products that can be made by this method are 6-(bromomethyl)-quinoxaline, 6-(chloromethyl)-quinoxaline, 5-(bromomethyl)-quinoxaline and 5-(chloromethyl)-quinoxaline. Other products that can be made by this method are: 4- and 5-(bromomethyl)-benzotriazole, 4- and 5-(chloromethyl)-benzotriazole, 4- and 5-(bromomethyl)-benzimidazolone, 4- and 5-(chloromethyl)-benzimidazolone. Other nitrogenous heterocyclic compounds that can be halogenated using this method include α- and γ-picoline, quinaldines, methylphenanthridine.

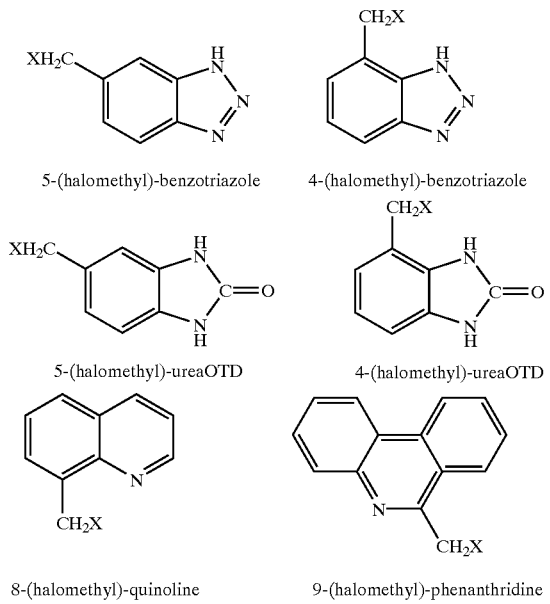

5-(halomethyl)-benzotriazole    4-(halomethyl)-benzotriazole 5-(halomethyl)-ureaOTD    4-(halomethyl)-ureaOTD 8-(halomethyl)-quinoline    9-(halomethyl)-phenanthridine In another specific embodiment, the present invention is directed to a halomethyl compound selected from the group consisting of:

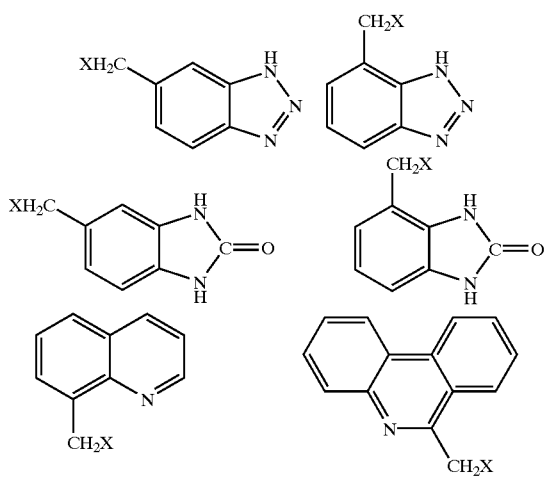

wherein X is a halogen.

Preferably the halomethyl compound is selected from the group consisting of:

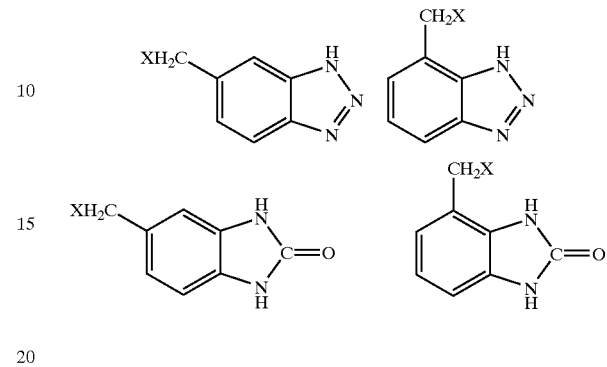

Throughout this disclosure, applicant will suggest various theories or mechanisms by which applicant believes the present methods function. While applicant may offer various mechanisms to explain the present invention, applicant does not wish to be bound by theory. These theories are suggested to better understand the present invention but are not intended to limit the effective scope of the claims.

The present invention is further illustrated by the following examples which are presented for purposes of demonstrating, but not limiting, the preparation of the compounds and compositions of this invention.

EXAMPLES

Examples 1–13

Table 1 is a summary of bromination reactions Examples 1–13.

TABLE 1

Summary for All Bromination Reactions.

| Solvent | [QX] | [NBS] | [BP] | [NBS]/[6Qx] | [6Qx]/[BP] | % Sel | % Conv. | Temp (° C.) | Time (hrs) | Comments |
|---|---|---|---|---|---|---|---|---|---|---|
| CH$_3$CN | 0.23 | 0.25 | 0.01 | 1.1 | 23 | ND | 98.5 | 83 | 4.0 | Example 1 |
| AcOH | 0.3 | 0.33 | 0.01 | 1.1 | 23 | ND | 99.1 | 115 | 1.0 | Example 1 |
| CH$_3$CN | 0.23 | 0.25 | 0.01 | 1.1 | 23 | NR | NR | 83 | 4.0 | Example 2 |
| 1,2-DCE | 0.31 | 0.34 | 2.2 10$^{-2}$ | 1.1 | 15 | 94 | 80 | 83 | 1.5 | Example 3 |
| 1,2-DCE | 0.39 | 0.44 | 1.8 10$^{-2}$ | 1.1 | 20 | ND | <2 | 70 | 1.0 | Example 4 |
| 1,2-DCE | 0.39 | 0.43 | 1.8 10$^{-2}$ | 1.1 | 20 | 85 | 60 | 83 | 2.0 | Example 5 Under N$_2$ |
| 1,2-DCE | 0.39 | 0.43 | 9.4 10$^{-3}$ | 1.1 | 43 | 70 | 37 | 83 | 1.8 | Example 6 #1 |
| 1,2-DCE | 0.31 | 0.35 | 2.2 10$^{-2}$ | 1.1 | 20 | 92 | 68 | 83 | 2.3 | Example 7 #2 |
| 1,2-DCE | 0.31 | 0.46 | 2.2 10$^{-2}$ | 1.5 | 14 | 93.4 | 85 | 83 | 2.5 | Example 8 |
| AcOH | 0.25 | 0.27 | 1.7 10$^{-2}$ | 1.1 | 14 | 85 | 43 | 113 | 0.75 | Example 9 |

TABLE 1-continued

Summary for All Bromination Reactions.

| Solvent | [QX] | [NBS] | [BP] | [NBS]/ [6Qx] | [6Qx]/ [BP] | % Sel | % Conv. | Temp (° C.) | Time (hrs) | Comments |
|---|---|---|---|---|---|---|---|---|---|---|
| AcOH | 0.25 | 0.27 | $1.7 \cdot 10^{-2}$ | 1.1 | 14 | <1 | 50 | 113 | 1.5 | Example 9 |
| n-heptane | 0.25 | 0.27 | $1.7 \cdot 10^{-2}$ | 1.1 | 14 | <1 | ND | 98 | 1.0 | Example 10 |
| Chlorobenzene | 0.31 | 0.46 | $2.2 \cdot 10^{-2}$ | 1.5 | 14 | 97 | 95 | 85 | 2.0 | Example 11 |
| Chlorobenzene | 0.31 | 0.46 | $2.2 \cdot 10^{-2}$ | 1.5 | 14 | 84 | 75 | 85 | 0.75 | Example 12 |
| 1,2-DCE | 0.31 | 0.35 | $2.2 \cdot 10^{-2}$ | 1.1 | 20 | 92 | 68 | 83 | 2.3 | Example 13 |

In a typical example (Example 11), 6-(methyl)-quinoxaline (1.25 g, 8.68 mmol) was dissolved together with N-bromosuccinimide (2.32 g, 13.0 mmol) and benzoyl peroxide (0.15 g, 0.62 mmol) in 31 g of chlorobenzene in a 50 ml flask. The yellow solution was heated to 85° C. with a water bath and maintained at this temperature for two hours.

During the benzylic halogenation of methyl-quinoxalines, ring halogenation can occur causing a significant decrease in the selectivities for the halomethyl-quinoxaline. Example 6 describes a reaction between N-bromosuccinimide and 6-(methyl)-quinoxaline in 1,2-dichloroethane under reflux. During the first hour, the selectivity for 6-(bromomethyl)-quinoxaline was 90.8% at 31% conversion. After 1.8 hours (110 minutes) the conversion increased to 37%, but the selectivity dramatically dropped to 70%. Further analysis of the sample revealed the presence of a compound containing the bromine atom attached to the aromatic ring. The selectivity for this undesired product increased from 3% (after 1 hour reflux) to 20% (after 1.8 hours reflux). Further reflux caused the selectivity for benzylic bromination to decrease even more (61% after 2.8 hours) with the expected increase in ring bromination (27% selectivity). Thus, the appropriate reaction time relates to the initiator half-life because heating the reaction mixture in the absence of radicals will favor the formation of ring brominated byproducts. A reaction time from 1 to 3 hours seems appropriate for benzylic brominations when benzoyl peroxide is used as radical initiator. A broader range may be applicable to benzylic chlorinations with N-chlorosuccinimide depending on the solvent (1 hour in chlorobenzene at 105° C. and 12 hours in acetonitrile at 82° C).

Typical yields are as follow: Bromination with N-bromosuccinimide of 6-(methyl)-quinoxaline to 6-(bromomethylquinoxaline): ~95% conversion and ~97% selectivity in chlorobenzene as solvent.

Examples 14–20

Table 2 is a summary of bromination reactions Examples 14-20.

TABLE 2

Summary for All Chlorination Reactions

| Solvent | [QX] | [NCS] | [BP] | [NCS]/ [6Qx] | [6Qx]/ [BP] | % Sel | % Conv. | Temp. (° C.) | Time (hrs) | Comments |
|---|---|---|---|---|---|---|---|---|---|---|
| $CH_3CN$ | 0.22 | 0.34 | $5.4 \cdot 10^{-3}$ | 1.5 | 40 | 80 | 60 | 82 | 12.0 | Example 14 |
| $CH_3CN$ | 0.85 | 1.29 | $1.2 \cdot 10^{-2}$ | 1.5 | 70 | ND | 20 | 82 | 6.0 | Example 15 |
| MTBE | 0.25 | 0.28 | $1.8 \cdot 10^{-2}$ | 1.1 | 14 | NR | NR | 56 | 4.0 | Example 16 |
| t-BuOH | 0.33 | 0.35 | $2.3 \cdot 10^{-2}$ | 1.1 | 14 | NR | NR | 83 | 4.0 | Example 16 |
| 1,2-DCE | 0.31 | 0.33 | $2.2 \cdot 10^{-3}$ | 1.1 | 14 | <15 | 15 | 83 | 1.2 | Example 16 |
| ACOH | 0.34 | 0.37 | $2.4 \cdot 10^{-2}$ | 1.1 | 14 | <1.6 | 1.6 | 80 | 2.0 | Example 16 |
| $CHCl_3$ | 0.30 | 0.33 | $2.2 \cdot 10^{-2}$ | 1.1 | 14 | trace | trace | 61 | 4.0 | Example 16 |
| $CF_3Ph$ | 0.34 | 0.52 | $2.0 \cdot 10^{-2}$ | 1.6 | 17 | 77 | 57 | 102 | 1.5 | Example 17 |
| ClPh | 0.34 | 0.52 | $2.0 \cdot 10^{-2}$ | 1.5 | 17 | ND | <1 | 85 | 1.0 | Example 18 |
| ClPh | 0.34 | 0.52 | $2.0 \cdot 10^{-2}$ | 1.5 | 17 | 78 | 50 | 105 | 1.0 | Example 19 |
| AcOH | 0.34 | 0.52 | $2.0 \cdot 10^{-2}$ | 1.5 | 17 | 83 | 48 | 115 | 0.75 | Example 20 |

In a typical example (Example 20), 6-(methyl)-quinoxaline (1.25 g, 8.68 mmol) was dissolved together with N-chlorosuccinimide (1.75 g, 13.1 mmol) and benzoyl peroxide (0.12 g, 0.49 mmol) in 27.7 g of chlorobenzene in a 50 ml flask. The reaction mixture was heated up to 105° C. for 3 hrs.

In non-polar solvents, such as n-heptane, no appreciable benzylic bromination of 6-(methyl)-quinoxaline was observed (<1%). For chlorinations, poor yields were obtained in hydrocarbon solvents such as tert-butyl methyl ether (MTBE), tert-butanol, heptane, 1,2-dichloroethane and chloroform. The poor benzylic chlorination yields are attributed to the poor stability of these solvents towards chlorine atoms.

In polar solvents, such as 1,2-dichloroethane, a good yield of 6-(bromomethyl)-quinoxaline was observed and consequently other hydrochlorocarbons (for example, methylene chloride) would be expected to be good as well. However, these solvents are less preferred due to their high toxicity and volatility. In other polar solvents, such as acetic acid, 5-(methyl)-quinoxaline reacted with N-bromosuccinimide almost quantitatively to give 5-(bromomethyl)-quinoxaline. However, the 6-isomer reacted to give 6-(bromomethyl)-quinoxaline that quickly decomposed to give a black tar.

Therefore, benzylic bromination with N-bromosuccinimide in acetic acid can only apply to one isomer (the 5-isomer) but not to the mixtures of 5- and 6-methylquinoxalines obtained from ortho-toluene diamine. In acetonitrile, the 5-isomer reacted with N-bromosuccinimide to give 5-(bromomethyl)-quinoxaline in a good yield (>90%) but the 6-isomer did not react. Therefore, benzylic bromination with N-bromosuccinimide in acetonitrile can only apply to one isomer (the 5-isomer) but not to the methylquinoxalines mixtures obtained from ortho-toluene diamine. An acceptable yield was obtained for the benzylic chlorination of 6-methyl-quinoxaline using N-chlorosuccinimide in acetonitrile (conversion=60% and selectivity=80%) but the reaction was very slow requiring 8 to 12 hours reflux (Example 15).

Best yields and reaction rates were obtained when benzylic halogenations of methyl-quinoxalines were carried out in chlorobenzene and $\alpha,\alpha,\alpha$-trifluoromethylbenzene. For example, chlorination of 6-methyl-quinoxaline with N-chlorosuccinimide in chlorobenzene or $\alpha,\alpha,\alpha$-trifluoromethylbenzene afforded 6-chloromethyl-quinoxaline with ~78% selectivity at 57% conversion. Similarly, bromination of 6-methyl-quinoxaline with N-bromosuccinimide in chlorobenzene gave 6-bromomethyl-quinoxaline with ~97% selectivity at 95% conversion. The advantages of using chlorobenzene are: a) in chlorobenzene, excellent yields are obtained for both benzylic chlorination and benzylic bromination; b) the vapor pressure of chlorobenzene is 10 times smaller than that of CCl4 [Chlorobenzene Vp=8.8 mm Hg and CCl4 Vp=91.3 mm Hg]; c) chlorobenzene is not classified as a human carcinogen (carbon tetrachloride is); d) chlorobenzene does not deplete the ozone layer; and e) chlorobenzene can be use to halogenate methyl-quinoxaline mixtures.

Benzylic halogenations are also expected to take place in good yields in similar solvents such as 1,2-dichlorobenzene (Vp=1.2 mm Hg at 20° C., mp.=−17° C.), 1,3-dichlorobenzene (Vp=5 mm Hg at 38.8° C., mp.=−24° C.) and 1,4-dichlorobenzene (Vp=0.4 mm Hg at 20° C., mp. 54–56° C.), trichlorotoluene (Vp=1 mm Hg @45.8° C.), fluorobenzene, difluorobenzenes and $\alpha,\alpha,\alpha$-trifluorobenzenes. Perfluorocarbons are also good solvents for benzylic halogenations.

Typical yields are as follow: Chlorination with N-chlorosuccinimide of 6-(methyl)-quinoxaline to 6-(chloromethylquinoxaline): ~60% conversion and ~80% selectivity in chlorobenzene as solvent.

Throughout this application, various publications have been referenced. The disclosures in these publications are incorporated herein by reference in order to more fully describe the state of the art.

1. R. Granger, S. Deadwyler, M. Davis, B. Moskovitz, M. Kessler, G. Rogers, G. Lynch, Synapse, 22, pp. 332–337, 1996; and (b) G. Lynch, M. Kessler, G. Rogers, J. Ambross-Ingerson, R. Granger, R. S. Schehr, International Clinical Psychopharmacology, 11, pp.13–19, 1996.

2. (a) J. Gum, J. Org. Chem., 30, 3982, 1965; (b) W. H. Huang, A. R. Lee, C. I. Lin, M. H. Yen, Yixue Yanjiu, 13, 247–54,1993.

3. B. Schilling, Ber., 34, pp. 902–907,1901.

4. (a) A. Tallec, Ann. Chim. (Paris), 3, 164, 1968; (b) V. Cere, D. Dal Monte, E. Sardi, Tetrahedron, 28, 3271, 1972.

5. M. Hudlicky "Oxidations in Organic Chemistry", ACS Monograph 186, 1990.

6. R. A. Sheldon, J. K. Kochi, "Metal-Catalyzed Oxidation of Organic Compounds", Chapter 5, pp. 121–151, Academic Press, 1981.

7. 2,3-Pyrazinedicarboxylic acid: "Organic Synthesis" Coll. Vol. 4 pp. 824–827, J. Wiley & Sons, Inc. N.Y., 1963.

8. R. A. Sheldon, J. K. Kochi, "Metal-Catalyzed Oxidation of Organic Compounds", Chapter 7, pp. 189–214, Academic Press, 1981.

9. J. C. Cavagnol, F. Y. Wiselogle, J. Am. Chem. Soc., 69, 795, 1947.

10. Thomas D. Waugh, NBS: N-Bromosuccinimide Its Reactions and Uses; Arapahoe Chemicals, Inc. Boulder Co. 1951.

11. D. F. Gavin, U.S. Pat. No. 3,690,963 (1976).

12. Benzoyl Piperidine: "Organic Synthesis", Coll. Vol. 1 pp. 108–110, J. Wiley & Sons, Inc. N.Y., 1943.

While a number of embodiments of this invention have been represented, it is apparent that the basic construction can be altered to provide other embodiments which utilize the invention without departing from the spirit and scope of the invention. All such modifications and variations are intended to be included within the scope of the invention as defined in the appended claims rather than the specific embodiments which have been presented by way of example.

What is claimed is:

1. A method for preparing 6-bromomethyl quinoxaline which comprises contacting 6-methyl quinoxaline with N-bromosuccinimide in the presence of a radical initiator in 1, 2-dichloroethane to form 6-bromomethyl quinoxaline.

* * * * *